United States Patent [19]

Nagabhushan

[11] 4,311,857
[45] Jan. 19, 1982

[54] 1-ARYL-2-ACYLAMIDO-3-FLUORO-1-PROPANOL ACYLATES, METHODS FOR THEIR MANUFACTURE AND INTERMEDIATES USEFUL THEREIN, METHODS FOR THEIR USE AS ANTIBACTERIAL AGENTS AND COMPOSITIONS USEFUL THEREFOR

[75] Inventor: Tattanahalli L. Nagabhushan, Parsippany, N.J.

[73] Assignee: Schering Corporation, Kenilworth, N.J.

[21] Appl. No.: 137,160

[22] Filed: Apr. 4, 1980

Related U.S. Application Data

[63] Continuation-in-part of Ser. No. 9,207, Feb. 5, 1979, Pat. No. 4,235,892.

[30] Foreign Application Priority Data

Jan. 28, 1980 [ZA] South Africa .................. 80/0478

[51] Int. Cl.$^3$ ................ C07D 209/34; C07C 87/28
[52] U.S. Cl. .................... 564/212; 260/326 N; 260/326 S; 260/326 HL; 260/349; 260/465 D; 564/84; 564/85; 564/86; 564/134; 564/137; 564/144; 564/145; 564/213; 564/219; 564/337; 564/355

[58] Field of Search .................. 564/337, 355, 85, 86, 564/134, 137, 144, 145, 213, 219, 212, 84; 260/465 D, 349, 326 HL, 326 S, 326 N

[56] References Cited

U.S. PATENT DOCUMENTS 3,012,073  5/1961  Gregory ........................... 564/212

OTHER PUBLICATIONS

Hahn Antibiotics, Springer–Verlag, N.Y., N.Y., (1967), p. 308.
Hahn et al., Antiobiotics and Chemotherapy, 6 (1956), p. 531.
Cima et al., Il Farmaco, Ed. Sc., 12 (1957), p. 535.
Mitsuhasi et al., Jap. J. Microbiol., 13 (1969), pp. 177–180.
Kono et al., Jap. J. Microbiol. 15 (1971), pp. 219–227.

*Primary Examiner*—Arthur P. Demers
*Attorney, Agent, or Firm*—Mary S. King

[57] ABSTRACT

Described are D-(threo)-1-aryl-2-acylamido-3-fluoro-1-propanol esters and salts thereof, methods for their preparation, and methods for their use as antibacterial agents.

7 Claims, No Drawings

1-ARYL-2-ACYLAMIDO-3-FLUORO-1-PROPANOL ACYLATES, METHODS FOR THEIR MANUFACTURE AND INTERMEDIATES USEFUL THEREIN, METHODS FOR THEIR USE AS ANTIBACTERIAL AGENTS AND COMPOSITIONS USEFUL THEREFOR

CROSS-REFERENCE TO RELATED APPLICATIONS

This application is a continuation-in-part of my copending application U.S. Ser. No. 9,207 filed Feb. 5, 1979, now U.S. Pat. No. 4,235,892.

FIELD OF INVENTION

This invention relates to novel compositions-of-matter, to methods for their preparation, and to methods for their use as antibacterial agents.

More specifically, this invention relates to novel 1-aryl-2-acylamido-3-fluoro-1-propanol antibacterial agents, to methods for their manufacture and to novel intermediates useful therein, to pharmaceutical compositions comprising said 1-aryl-2-acylamido-3-fluoro-1-propanols and to methods for their use in treating antibacterial infections.

In particular, this invention relates to D-(threo)-1-phenyl (or para- and/or meta-substituted-phenyl)-2-alkanoylamido (or 2-halogenoalkanoylamido or 2-azidoalkanoylamido or 2-methylsulfonylacetamido)-3-fluoro-1-propanol antibacterial agents, including the 3-fluoro-3-deoxy derivatives of chloramphenicol, of the difluoroacetyl analog of chloramphenicol, of thiamphenicol, fluorthiamphenicol, tevenel, and fluortevenel (i.e., the difluoroacetyl analog of tevenel), and to 1-hydrocarboncarboxylate (preferably 1-carboxyhydrocarboncarboxylate) esters and 1-(aminohydrocarboncarboxylate) esters and their pharmaceutically acceptable salts, methods for their preparation and for their use as antibacterial agents.

PRIOR ART

Known in the art are broad spectrum antibiotics which may be classified as D-(threo)-1-p-substituted phenyl-2-halogenoacetylamido-1,3-propanediols, including chloramphenicol (D-(threo)-1-p-nitrophenyl-2-dichloroacetamido-1,3-propanediol), thiamphenicol (D-(threo)-1-p-methylsulfonylphenyl-2-dichloroacetamido-1,3-propanediol), fluorthiamphenicol (D-(threo)-1-p-methylsulfonylphenyl-2-difluoroacetamido-1,3-propanediol) and tevenel (D-(threo)-1-p-aminosulfonylphenyl-2-dichloroacetamido-1,3-propanediol).

Also known in the art is that any structural modification of the primary hydroxyl group at C-3 of chloramphenicol, including replacement of the hydroxyl group by chlorine or bromine, destroys the biological activity thereof (F. E. Hahn, *Antibiotics*, Ed. Gottlieb and Shaw, Springer-Verlag, New York, (1967), p. 308; F. E. Hahn et al, *Antibiotics and Chemotherapy*, 6, No. 9, 531 (1956); L. Cima and A. Ilecto, *Il Farmaco*, Ed. Sc. 12, No. 6, 535 (1957); S. Mitsuhasi et al, *Jap. J. Microbiol.* 13, No. 2, 177–80 (1969); K. Megaim et al, *Jap. J. Microbiology* 15 (3), 219–27 (1971)).

Heretofore unknown in the art were derivatives of D-(threo)-1-p-substituted-phenyl-2-halogenoalkanoylamido-1,3-propanediols in which the 3-hydroxyl group was replaced by fluorine.

By my invention, I have developed methods for preparing novel D-(threo)-1-phenyl (or para and/or meta-substituted phenyl)-2-alkanoylamido (or 2-halogenoalkanoylamido or 2-azidoalkanoylamido or 2-methylsulfonylacetamido)-3-fluoro-1-propanols and have found that, surprisingly, these 3-fluoro- derivatives are broad spectrum antibacterial agents useful in the treatment of gram positive, gram negative, and rickettsial infections. I have also discovered that the 3-fluoro-3-deoxy derivatives of chloramphenicol and of thiamphenicol are advantageously and unexpectedly cidal against bacteria resistant to chloramphenicol and thiamphenicol as well as against bacteria which are susceptible to these parent antibiotics.

GENERAL DESCRIPTION OF THE INVENTION

Composition-of-Matter Aspect

Included among the antibacterially active compositions-of-matter of this invention are D-(threo)-1-aryl-2-acylamido-3-fluoro-1-propanol acylates of the following formula I:

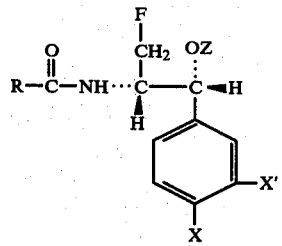

wherein R is a member selected from the group consisting of methyl or ethyl or a halogenated derivative thereof, dihalogenodeuteriomethyl, 1-halogeno-1-deuterioethyl, 1,2-dihalogeno-1-deuterioethyl, azidomethyl and methylsulfonylmethyl; each of X and X' is a member selected from the group consisting of $NO_2$, $SO_2R_1$, $SOR_1$, $SR_1$, $SONH_2$, $SO_2NH_2$, $SONHR_1$, $SO_2NHR_1$, $COR_1$, $OR_1$, $R_1$, $CN$, halogen, hydrogen, phenyl and phenyl substituted by halogen, $NO_2$, $SO_2CH_3$, $R_1$ or $OR_1$, wherein $R_1$ is methyl, ethyl, n-propyl or isopropyl;

and Z is hydrogen or an acyl radical of a hydrocarboncarboxylic acid (preferably a hydrocarbondicarboxylic acid) having up to 16 carbon atoms or an acyl radical of an amino hydrocarboncarboxylic acid having up to 12 carbon atoms; and the pharmaceutically acceptable salts of said acyl radicals.

Included among the halogenated alkyl groups contemplated for the moiety R in this invention are the mono-, di- and tri-fluoro-, the mono-, di- and tri-chloro-, the mono- and di-bromo-, and the iodo-methyl groups as well as the mono- and di-fluoro-, the mono- and di-chloro-, the mono- and di-bromo-, and the iodoethyl groups wherein the halogen substituents are preferably on the carbon alpha to the carbonyl function. Also included are mixed dihalogenoalkyl groups in which both halogens are preferably bonded to the carbon alpha to the carbonyl groups, e.g., groups such as fluorochloro-, fluorobromo-, and chlorobromo-methyl and ethyl, as well as trihalogenomethyl groups such as dichlorofluoro- and difluorochloro-methyl. Additionally, among the halogenated alkyl group, R, are included those having a deuterio atom on the carbon alpha to the carbonyl function, e.g., dihalogenodeuteriomethyl groups such as dichlorodeuterio-, difluorodeuterio- and chlorofluorodeuterio-methyl, as well as 1-halogeno-1-deuterioethyl groups such as 1-fluoro-1-deuterio- and 1-chloro-1-deuterioethyl and 1,2-dihalogeno-1-deuterioethyl groups such as 1,2-dichloro-1-deuterio- and 1,2-difluoro-1-deuterio-ethyl. Thus, the 2-acylamido groups contemplated by this invention (i.e.,

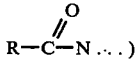

include mono-, di-, and tri-halogeno-acetamido derivatives as well as α-halogenopropionamido, β-halogenopropionamido-, and α,α- and α,β-dihalogenopropionamido derivatives and deuterio derivatives thereof. Of the foregoing, preferred are compounds of formula I wherein

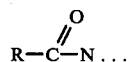

is dichloroacetamido, difluoroacetamido, fluorochloroacetamido, and deuterio derivatives thereof.

Of the 1-phenyl derivatives of formula I contemplated by this invention, preferred are the p-substituted phenyl groups (i.e., compounds of formula I wherein X' is hydrogen), particularly the 1-p-nitrophenyl (i.e. X is $NO_2$), the 1-p-methylsulfonylphenyl (i.e. X is $SO_2CH_3$), the 1-p-aminosulfonylphenyl (i.e. X is $SO_2NH_2$), and the 1-p-methylsulfinylphenyl (i.e. X is $SOCH_3$).

The compounds of formula I have two assymetric centers at carbons 1 and 2 of the propanol structure and, therefore, have four possible stereoisomers. The preferred stereoisomer of my invention is the one in which the absolute configuration is D and the relative configuration is threo. Thus, the compounds defined by formula I have the D-(threo)- configuration, which is the same isomeric form present in the prior art antibiotics chloramphenicol and the difluoroacetyl analog thereof, thiamphenicol, fluorthiamphenicol, and tevenel.

In addition to the foregoing, when R is a mixed diahlogenomethyl or a 1-halogenoethyl or a deuterio derivative thereof, an assymetric center exists within the acylamido group

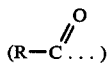

at the carbon to which the halogen is bonded. It is to be understood that both stereoisomeric forms within the acylamido group as well as racemates thereof are included within the concept of my invention.

Of particular interest are compounds of formula I having a 1-p-nitrophenyl or a 1-p-methylsulfonylphenyl group and a 2-dichloroacetamido or a 2-difluoroacetamido or a 2-(chlorofluoroacetamido) group or deuterio derivatives thereof, which are the 3-fluoro-3-deoxy derivatives of chloramphenicol and the difluoroacetyl analog thereof, thiamphenicol and fluorthiamphenicol, and of their corresponding 2-(chlorofluoroacetamido) derivatives thereof and of their deuterio derivatives. These are D-(threo)-1-p-nitrophenyl-2-dichloroacetamido-3-fluoro-1-propanol (R=$Cl_2CH$; X=$NO_2$; X'=H); and its deuterio derivative (R=$Cl_2CD$); D-(threo)-1-p-nitrophenyl-2-difluoroacetamido-3-fluoro-1-propanol (R=$F_2CH$; X=$NO_2$; X'=H) and its deuterio derivative (R=$F_2CD$); D-(threo)-1-p-methulsulfonylphenyl-2-dichloroacetamido-3-fluoro-1-propanol (R=$Cl_2CH$; X=$SO_2CH_3$; X'=H) and its deuterio derivative (R=$Cl_2CD$); D-(threo)-1-p-methylsulfonylphenyl-2-difluoroacetamido-3-fluoro-1-propanol (R=$F_2CH$; X=$SO_2CH_3$; X'=H) and its deuterio derivative (R=$Cl_2CD$); and the 2-(chlorofluoroacetamido) analogs of the foregoing and their deuterio derivatives, e.g., D-(threo)-1-p-nitrophenyl-2-(R,S-chlorofluoroacetamido)-3-fluoro-1-propanol (R=ClFCH; X=$NO_2$; X'=H) and its deuterio derivative (R=ClFCD). The foregoing compounds advantageously have antibacterial activity against organisms resistant to, as well as against organisms susceptible to, their precursor 3-hydroxy antibiotics. Thus, these compounds are broad spectrum antibacterial agents having a broader spectrum of activity than chloramphenicol or thiamphenicol, and are useful in the treatment of gram positive, gram negative and rickettsial infections.

Other valuable broad spectrum antibacterial agents of formula I include:

D-(threo)-1-p-aminosulfonylphenyl-2-dichloroacetamido-3-fluoro-1-propanol (R is $Cl_2CH$—; X is $NH_2SO_2$; X' is H, a derivative of tevenel);

D-(threo)-1-p-aminosulfonylphenyl-2-difluoroacetamido-3-fluoro-1-propanol (R is $F_2CH$—; X is $NH_2SO_2$; X' is H, a derivative of fluortevenel);

D-(threo)-1-p-methylsulfinylphenyl-2-dichloroacetamido-3-fluoro-1-propanol (R=$Cl_2CH$; X=$SOCH_3$; X'=H);

D-(threo)-1-p-methylsulfinylphenyl-2-difluoroacetamido-3-fluoro-1-propanol (R=$F_2CH$; X=$SOCH_3$; X'=H);

D-(threo)-1-p-nitrophenyl-2-methylsulfonylacetamido-3-fluoro-1-propanol (R=$CH_3SO_2CH_2$; X=$NO_2$; X'=H); and D-(threo)-1-p-nitrophenyl-2-azidoacetamido-3-fluoro-1-propanol (R=$N_3CH_2$; X=$NO_2$; X'=H).

Also included among the antibacterially active compounds of this invention are the ester derivatives, e.g. 1-hydrocarboncarboxylates of formula I wherein Z is an acyl radical of a hydrocarboncarboxylic acid having up to 16 carbon atoms which may be saturated, unsaturated, straight chain or branched chain, aliphatic, cyclic, cyclic-aliphatic, aromatic, aryl-aliphatic, or alkyl-aromatic and may be substituted by hydroxy, alkoxy containing from 1 to 5 carbon atoms, carboxyl or halogen. The 1-hydrocarboncarboxylates of the D-(threo)-1-aryl-2-acylamido-3-fluoro-1-propanols of my invention are thus derived from hydrocarboncarboxylic acids such as alkanoic acids exemplified by formic, acetic, propionic, trimethylacetic, butyric, isobutyric, valeric, isovaleric, caproic, tert.-butylacetic, enanthic, caprylic, capric, cyclopentylpropionic, undecylic, lauric, palmitic, and adamantanecarboxylic acids; substituted alkanoic acids such as phenoxyacetic, trifluoroacetic, β-chloropropionic and pantothenic acids; aromatic and substituted aromatic acids including benzoic, toluic, p-chlorobenzoic, p-fluorobenzoic, p-methoxybenzoic, and 3',5'-dimethylbenzoic acids; aryl-alkanoic acids such as phenylacetic, phenylpropionic, and β-benzoylaminoisobutyric acids; unsaturated acids such as acrylic, cinnamic, and sorbic acids; and, preferably, dibasic acids such as succinic, tartaric, and phthalic acids.

Other antibacterially active ester derivatives of formula I are those wherein Z is an acyl radical of an amino acid containing up to 12 carbon atoms and which may be saturated, unsaturated, straight chain, branched chain or cyclic, which may contain aromatic groups and which may be substituted by hydroxyl groups. Amino acid ester derivatives of formula I are thus compounds wherein Z is derived from a neutral amino acid such as tryptophan, threonine, serine, hydroxyproline, proline, tyrosine, phenylalanine, isoleucine, leucine, valine, alanine, and, preferably, glycine. Amino acid ester derivatives of Formula I are also derived from basic amino acids such as diaminobutyric acid, ornithine, and lysine.

Preferred ester derivatives of my invention include those derived from dibasic hydrocarboncarboxylates, e.g. the 1-succinate and 1-palmitate esters, which provide water soluble, pharmaceutically acceptable cationic salts, e.g. the sodium or potassium salts, as well as salts with an amine, e.g. trimethylamine. Also preferred are ester derivatives of amino acids which provide water soluble, pharmaceutically acceptable acid addition salts with mineral or organic acids, e.g. the hydrochloric, or sulfuric acid, or the succinic acid addition salts.

The term "pharmaceutically acceptable salts" of this invention thus includes salts wherein the acidic hydrogen in the dibasic hydrocarbcarboxylate esters of this invention is replaced with a cation (e.g. sodium D-(threo)-1-p-nitrophenyl-2-dichloroacetamido-3-fluoro-1-propyl hemisuccinate) as well as salts wherein the acidic hydrogen forms an acid addition salt with an amine (e.g. D-(threo)-1-p-nitrophenyl-2-dichloroacetamido-3-fluoro-1-propyl hemisuccinate N-trimethylamine salt). Also included in the term "pharmaceutically acceptable salts" are the acid addition salts formed between mineral or organic acids and the amine in the amino acid esters of this invention (e.g. D-(threo)-1-p-nitrophenyl-2-dichloroacetamido-3-fluoro-1-propyl glycinate hydrochloride).

Among the pharmaceutically acceptable cationic salts of the dibasic hydrocarboncarboxylate esters contemplated for this invention are salts of alkali and alkaline earth metals (e.g. sodium, potassium, calcium, aluminum) and salts with an amine such as trialkylamines, procaine, dibenzylamine, N-benzyl-beta-phenethylamine, N,N'-dibenzylethylenediamine, N,N'-bisdehydroabietylethylenediamine, N-(lower)alkylpiperidines (e.g. N-ethylpiperidine), and N-methyl glucamine.

The pharmaceutically acceptable cationic salts (e.g. the sodium salt or trimethylamine salt) are prepared according to known procedures such as by combining equimolar quantities of the corresponding base (e.g. sodium hydroxide or trimethylamine) to the dibasic hydrocarboncarboxylate ester derivative (e.g. D-(threo)-1-p-nitrophenyl-2-dichloroacetamido-3-fluoro-1-propylhemisuccinate) in an aqueous solution and lyophilizing the resultant solution of the dibasic hydrocarboncarboxylate salt (e.g. sodium D-(threo)-1-p-nitrophenyl-2-dichloroacetamido-3-fluoro-1-propyl hemisuccinate or D-(threo)-1-p-nitrophenyl-2-dichloroacetamido-3-fluoro-1-propyl hemisuccinate trimethylamine salt).

The pharmaceutically acceptable acid addition salts of the 1-propyl amino acid ester derivatives of this invention (e.g. D-(threo)-1-p-nitrophenyl-2-dichloroacetamido-3-fluoro-1-propyl glycinate hydrochloride) are made according to known procedures such as by neutralizing the free base (e.g. D-(threo)-1-p-nitrophenyl-2-dichloroacetamido-3-fluoro-1-propyl glycinate) with an appropriate acid (e.g. hydrochloric acid) to about pH 5. Suitable acids for this purpose include acids such as hydrochloric, sulfuric, phosphoric, nitric, hydrobromic, acetic, propionic, maleic, ascorbic, citric and the like. A preferred amino acid ester, Z, is derived from an α-amino acid such as glycine. Preferred acid addition salts of the glynate esters are the glycinate hydrochloride and sulfate salt.

The physical embodiments of the pharmaceutically acceptable salts of this invention are characterized by being white or off-white solids which are soluble in water, sparingly soluble in most polar solvents, and insoluble in most non-polar organic solvents.

The D-(threo)-1-phenyl (and m and/or p-substituted phenyl)-2-alkanoylamido (and halogenoalkanoylamido)-3-fluoro-1-propanol derivatives of this invention such as defined by formula I including the non-toxic, pharmaceutically acceptable salts thereof, in general, exhibit broad spectrum antibacterial activity and possess improved antibacterial activities compared to the parent antibiotics, i.e. to the corresponding compounds containing a 3-hydroxyl function instead of a 3-fluoro. This improved activity, particularly that of the D-(threo)-1-p-nitrophenyl- and the D-(threo)-1-p-methylsulfonylphenyl- derivatives is specifically manifest in the enhanced activity of the claimed 3-fluoro compounds against organisms resistant to the precursor 3-hydroxy compounds. Thus, for example, the compounds of this invention, as defined by formula I, particularly the D-(threo)-1-p-nitrophenyl- and D-(threo)-1-p-methylsulfonylphenyl-2-dichloroacetamido-3-fluoro-1-propanols as well as the corresponding 2-difluoroacetamido and 2-chlorofluoroacetamido analogs and deuterio derivatives thereof are more active against organisms which inactivate the parent antibiotics by O-acetylation of the 3-hydroxy group or by O-acetylation of both the 1- and 3-hydroxyl groups. Additionally, the compounds of formula I are also active against organisms which are sensitive to the parent organisms. In brief, the antibacterial compounds of formula I are active against organisms resistant to chloramphenicol and thiamphenicol while still retaining activity against organisms sensitive to chloramphenicol.

Particularly useful compounds of my invention are those wherein R is halogenomethyl, particularly dichloromethyl, difluoromethyl and chlorofluoromethyl and deuterio derivatives thereof, and wherein X' is hydrogen and X is aminosulfonyl, methylsulfinyl, and preferably nitro or methylsulfonyl. Of these, a particularly valuable group are the D-(threo)-1-p-nitrophenyl- and the D-(threo)-1-p-methylsulfonylphenyl derivatives of formula I, particularly the 2-dichloroacetamido-, 2-difluoroacetamido, and 2-chlorofluoroacetamido derivatives thereof and their deuterio derivative, which are broad spectrum antibiotics, being active against gram positive bacteria (e.g. *Staphylococcus aureus*) and gram negative bacteria (e.g. *Escherichia coli, Hemophilus influenzae,* Klebsiella, Salmonella, Shigella, Proteus, Enterobacter, and Serratia) as determined by standard dilution tests, including bacteria resistant to the 3-hydroxy analog precursor antibiotics, chloramphenicol and thiamphenicol and their 2-difluoroacetamido and 2-chlorofluoroacetamido counterparts including their deuterio derivatives.

Particularly useful antibacterials of this invention are D-(threo)-1-p-nitrophenyl-2-dichloroacetamido-3- fluoro-1-propanol; D-(threo)-1-p-nitrophenyl-2-difluoroacetamido-3-fluoro-1-propanol; D-(threo)-1-p-methylsulfonylphenyl-2-dichloroacetamido-3-fluoro-1-propanol; and D-(threo)-1-p-methylsulfonylphenyl-2-difluoroacetamido-3-fluoro-1-propanol, the corresponding 2-(R,S-chlorofluoroacetamido) derivatives thereof and the corresponding 2-(dihalogenodeuterioacetamido) derivatives of the foregoing.

Particularly useful ester derivatives of the compounds of the invention are the hemisuccinate esters particularly in the form of the sodium and trimethylamine cationic salts, and the glycinate ester particularly in the form of its hydrochloride or sulfate acid addition salt. As specifically preferred ester derivatives, there may be mentioned the sodium and trimethylamine salts of D-(threo)-1-p-nitrophenyl-2-dichloroacetamido-3-fluoro-1-propyl hemisuccinate and the hydrochloride and sulfate acid addition salts of D-(threo)-1-p-nitrophenyl-2-dichloroacetamido-3-fluoro-1-propyl glycinate. The pharmaceutically acceptable salts of the specified compounds of the general formula I, such as the aforementioned salts, are usually white or off-white solids which are generally soluble in water, sparingly soluble in polar solvents and insoluble in non-polar solvents.

Another composition-of-matter aspect of my invention are D-(threo)-1-aryl-2-amino-3-fluoro-1-propanols of formula II:

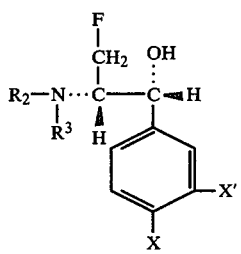

wherein X and X' are as defined for formula I and $R_2$ and $R_3$ are hydrogen or together form an amino protecting group.

The amino protecting groups ($R_2$ and $R_3$ together) contemplated for the compounds of formula II are preferably imido derivatives of dicarboxylic acids such as succinimido and, preferably, phthalimido.

The compounds of formula II are valuable as intermediates in preparing the antibacterially active compounds of formula I disclosed hereinabove as described in the process aspect of this invention disclosed hereinbelow.

PROCESS ASPECT OF THE INVENTION

The process aspect of this invention resides in the concept of the process for the preparation of a D-(threo)-1-aryl-2-acylamido-3-fluoro-1-propanol of formula I which comprises the reaction of D-(threo)-1-aryl-2-N-protected-amino-1,3-propanediol with dialkylamine sulfur trifluoride in an inert organic solvent followed by removal of the N-protecting group in the thereby formed D-(threo)-1-aryl-2-N-protected-amino-3-fluoro-1-propanol; thence reaction of the resulting D-(threo)-1-aryl-2-amino-3-fluoro-1-propanol with a lower alkanoic acid derivative such as alkanoic acid chloride or anhydride in the presence of a base and, in the case of the α,α-dihalogeno alkanoic acids, even with a lower alkyl ester in a lower alkanol.

The D-(threo)-1-aryl-2-amino-1,3-propanediol, precursors for the N-protected starting compounds of this process, are either known compounds or are conveniently prepared according to known procedures. Thus, for example, D-(threo)-1-p-methylsulfonylphenyl-2-amino-1,3-propanediol is conveniently prepared via acid hydrolysis of thiamphenicol (i.e. D-(threo)-1-p-methylsulfonylphenyl-2-dichloroacetamido-1,3-propanediol.

The 2-N-protected amino starting compound of my process prepared according to procedures well known in the art.

In the first step of my process, wherein the primary 3-hydroxyl- function in a D-(threo)-1-aryl-2-N-protected amino-1,3-propanediol is first selectively replaced by fluorine, the fluorinating agent of choice is a dialkylamine sulfur trifluoride, preferably diethylamine sulfur trifluoride. Other fluorinating agents which may be used in my process are sulfur trifluoride morpholine, sulfur trifluoride piperidine and other stable sulfur trifluoride-secondary amine adducts.

This step is conveniently carried out at temperatures in the range of −10° to +50° C., preferably at 0° C. in an inert organic solvent. By "inert organic solvent" is meant any organic or inorganic solvent in which the D-(threo)-1-aryl-2-protected amino-1,3-propanediol starting compounds and the reagents are reasonably soluble, and which will not interfere with the process under the reaction conditions thereof so there are produced a minimum of competing side reactions. The first step of our process is preferably carried out in an aprotic solvent, e.g. tetrahydrofuran, dioxane, or tetrahydropyran.

After removal of the N-protecting group utilizing known techniques (such as removal of a phthalimido group with hydrazine hydrate) the second step of my process comprises converting the unprotected 2-amino function to a 2-alkanoylamido function by reaction thereof with a lower alkanoic acid derivative selected from acetic acid anhydride or chloride, or propionic acid anhydride or chloride in the presence of base, or, in the case of halogeno acetic acids or halogeno propionic acids, with a lower alkyl ester of said halogeno alkanoic acids in a lower alkanol (e.g. an alkanol having up to 4 carbon atoms) said alkanoic acid derivatives being known compounds or conveniently prepared by known techniques.

Compounds of formula I wherein R is a halogenodeuterioalkyl are prepared from the corresponding compound of formula I wherein R is halogenoalkyl utilizing conventional deuterium exchange reactions, e.g., utilizing methyl alcohol-D (i.e. CH$_3$OD).

A preferred species of my process is that whereby a D-(threo)-1-aryl-2-amino-1,3-propanediol is first converted to the corresponding 2-N-protected derivative and then to the corresponding 1-aryl-2-N-protected-amino-3-fluoro-1-propanol by replacement of the primary 3-hydroxyl with fluorine, after which the 2-amino function is liberated and then converted to a 2-acetamido or 2-propionamido function or to halogeno derivatives thereof, i.e. a D-(threo)-1-aryl-2-N-substituted amino-3-fluoro-1-propanol. Thus, D-(threo)-1-p-nitrophenyl-2-phthalimido-1,3-propanediol is dissolved in an aprotic solvent (e.g. tetrahydrofuran) and reacted with an equimolar quantity of a dialkylamine sulfur trifluoride (e.g. diethylamine sulfur trifluoride) at temperatures in the range of from about 0° C. to room temperatures whereby is prepared a 3-fluoro-1-propanol derivative (e.g. D-(threo)-1-p-nitrophenyl-2- phthalimido-3-fluoro-1-propanol) which is conveniently isolated and purified utilizing conventional techniques, usually chromatographic methods. Removal of the N-protecting group (e.g. phthalimido) is then effected via known techniques (e.g. hydrazine hydrate in ethanol) and the resulting D-(threo)-1-aryl-2-amino-3-fluoro-1-propanol (e.g. D-(threo)-1-p-nitrophenyl-2-amino-3-fluoro-1-propanol) is converted to the corresponding 2-acetylamido derivative (e.g. 2-dichloroacetamido), by reaction with a halogeno alkanoic acid alkyl ester in an alkanol (e.g. methyl dichloroacetate in methanol) at elevated temperatures (usually at about 60° to 100° C.). Isolation and purification of the D-(threo)-1-aryl-2-acylamido-3-fluoro-1-propanol of formula I is then conveniently isolated by removing the solvents and treating the residue to extraction and chromatographic and crystallization methods.

Alternatively, the D-(threo)-1-aryl-2-acylamido-3-fluoro-1-propanols of formula I are prepared from the corresponding 3-oxazolidine of following formula III with hydrogen fluoride in the presence of fluoride ion, e.g. in the presence of lithium fluoride:

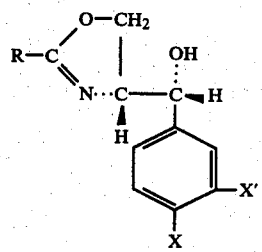

III wherein X, X' and R are as defined for formula I.

The oxazolidines of formula III may be prepared according to known methods. Alternatively, the oxazolidines are prepared by reacting a D-(threo)-1-aryl-2-acylamido-1,3-propanediol (e.g. chloramphenicol) with either trifluoromethylsulfonyl chloride in pyridine or p-toluenesulfonyl chloride in pyridine. In the latter case, the initial product is the 3-p-toluenesulfonate ester which cyclizes to the oxazolidine structure upon treatment with a base in a solvent.

Another method of preparing compounds of formula I comprises utilizing a starting material differing from the desired product in having in one or both of the para- and meta- positions of the phenyl moiety a substituent X'' which is a precursor of X or X' and thence converting X'' into the desired value of X or X'. For example, compounds of formula I wherein X' is hydrogen and X is —$SOR_1$ or —$SO_2R_1$ may be obtained by oxidation of the corresponding compound (which contains instead of the X substituent another substituent, X''', which is —$SR_1$ and $SOR_1$, respectively), utilizing oxidizing agents and conditions commonly employed in the conversion of an aryl thio-ether group into sulfinyl, e.g., utilizing sodium metaperiodate, or for the conversion of an aryl sulfinyl group into sulfonyl.

Compounds of formula I wherein Z is an acyl radical are preferably prepared by appropriate esterification of the corresponding compound of formula I in which Z is hydrogen, the so-obtained ester being isolated as such or where appropriate in the form of a pharmaceutically acceptable salt.

PHARMACEUTICAL COMPOSITION AND METHOD-OF-USE

Aspects of the Invention

The present invention includes within its scope the concept of a pharmaceutical composition comprising a D-(threo)-1-aryl-2-acylamido-3-fluoro-1-propanol of formula I together with a compatible, pharmaceutically acceptable carrier or coating.

Also included within this invention is the concept of the method of eliciting an antibacterial response in a warm-blooded animal having a susceptible bacterial infection which comprises administering to said animal a non-toxic, antibacterially effective amount of a D-(threo)-1-aryl-2-acylamido-3-fluoro-1-propanol of formula I.

As discussed hereinabove, the D-(threo)-1-aryl-2-acylamido-3-fluoro-1-propanols of formula I are broad spectrum antibacterial agents which, advantageously, exhibit activity against organisms which are resistant to their 3-hydroxy precursors. Thus, the compounds of this invention can be used alone or in combination with other antibiotic agents to prevent the growth or reduce the number of bacteria in various environments. They may be used, for example, to disinfect laboratory glassware, dental and medical equipment contaminated with *Staphylococcus aureus* or other bacteria inhibited by the 3-fluoro-1-propanols of this invention. The activity of the D-(threo)-1-aryl-2-acylamido-3-fluoro-1-propanols renders them useful for combatting infections caused by gram negative organisms, e.g. species of Proteus and Salmonella or by gram positive organisms, e.g. *Staphylococcus aureus*, and by Ricksettial organisms.

In general, the dosage of D-(threo)-1-aryl-2-acylamido-3-fluoro-1-propanol will be dependent on the age and weight of animal species being treated, the mode of administration, and the type and severity of bacterial infection being prevented or reduced. In general, the dosage of D-(threo)-1-aryl-2-acylamido-3-fluoro-1-propanol employed to combat a given infection will be similar to the dosage requirements of the corresponding 3-hydroxy analog or of chloramphenicol. Additionally, the D-(threo)-1-aryl-2-acylamido-3-fluoro-1-propanols of formula I, e.g. D-(threo)-1-p-nitrophenyl-2-dichloroacetamido-3-fluoro-1-propanol and the corresponding 1-p-methylsulfonylphenyl compound, are also advantageously cidal against certain organisms which are resistant to the corresponding 3-hydroxy precursor, i.e. which are resistant to chloramphenicol and to thiamphenicol.

The D-(threo)-1-aryl-2-acylamido-3-fluoro-1-propanols of formula I and the pharmaceutically acceptable salts of esters thereof may be administered parenterally, orally and topically.

The antibacterials of this invention may be utilized in liquid form such as solutions, suspensions, and the like for otic and optic use and may also be administered parenterally via intramuscular injection. The injectable solution or suspension will usually be administered at from about 1 mg. to about 15 mgs. of antibacterial per kilograms of body weight per day divided into about 2 to about 4 doses. The precise dose depends on the stage and severity of the infection, the susceptibility of the infecting organism to the antibacterial and the individual characteristics of the animal species being treated.

For oral administration, the D-(threo)-1-aryl-2-acylamido-3-fluoro-1-propanol antibacterials may be compounded in the form of tablets, capsules, elixirs or the like or may even be admixed with animal feed. It is in these dosage forms that the antibacterials are most effective for treating bacterial infections of the gastrointestinal tract which infections cause diarrhea.

The D-(threo)-1-aryl-2-acylamido-3-fluoro-1-propanols may also be applied topically in the form of ointments, both hydrophilic and hydrophobic, in the form of lotions which may be aqueous, non-aqueous or of the emulsion type or in the form of creams. Pharmaceutical carriers useful in the preparation of such formulations will included, for example, such substances as water, oils, greases, polyesters, polyols and the like.

In general, the topical preparations will contain from about 0.1 to about 3 gms. of D-(threo)-1-aryl-2-acylamido-3-fluoro-1-propanol of formula I per 100 gms. of ointment, cream or lotion. The topical preparations are usually applied gently to lesions from about 2 to 5 times a day.

FORMULATIONS

The following formulations are to exemplify some of the dosage forms in which the antibacterial agents of this invention may be employed. In each, the active ingredient is designated by the term "Drug" which is meant to indicate one of the following compounds.

D-(threo)-1-p-nitrophenyl-2-dichloroacetamido-3-fluoro-1-propanol; D-(threo)-1-p-methylsulfonylphenyl-2-dichloroacetamido-3-fluoro-1-propanol; and D-(threo)-1-p-methylsulfonylphenyl-2-difluoroacetamido-3-fluoro-1-propanol. It will be appreciated, however, that each of these compounds may be replaced by equally effective quantities of other compounds defined by formula I.

| Formulation 1 Oral Suspension | |
|---|---|
| | mg/ml |
| Drug, Micronized | 20.0 |
| Sorbitol solution, USP | 250.0 |
| Methylparaben, USP | 0.5 |
| Propylparaben, USP | 0.1 |
| Propylene Glycol, USP | 50.0 |
| Veegum HU (Mg-Aluminum Silicate) | 10.0 |
| Sodium Carboxymethylcellulose | 5.0 |
| Pluronic F-68 | 0.2 |
| Flavor (sufficient) | |
| Purified Water, USP qs ad | 1 ml |

MANUFACTURING PROCEDURE

Disperse the Veegum and Sodium carboxymethylcellulose in hot water (80° C.). Add the Sorbitol solution with stirring, followed by the micronized drug. Add the Pluronic F-68 previously dissolved in a portion of hot water (80° C.). Cool the batch to 30° C. Dissolve the Methyl and Propylparaben in the Propylene Glycol. Add the solution to the batch. Add the flavors to the batch. Mix until homogenous.

| Formulation 2 Ointment | |
|---|---|
| | mg/g |
| Drug, Micronized | 20.0 |
| Mineral Oil, USP | 50.0 |
| White Petrolatum, USP qs ad | 1.0 of g. |

MANUFACTURING PROCEDURE

Heat the weighed quantity of White Petrolatum and Mineral Oil to 65° and mix until uniform. Cool mixture to 50°-55° C. with stirring. The drug which has been dispersed in a portion of the Mineral Oil and milled, is added to the remainder of the base with stirring. The ointment is cooled to room temperature.

| Formulation 3 Cream | |
|---|---|
| | mg/g |
| Drug, Micronized | 20.0 |
| White Petrolatum, USP | 150.0 |
| Mineral Oil, USP | 50.0 |
| Cetomacrogol 1000 | 22.0 |
| Cetyl Alcohol | 40.0 |
| Stearyl Alcohol, USP | 40.0 |
| Sodium Phosphate, Monobasic | 4.0 |
| Propylene Glycol, USP | 50.0 |
| Purified Water qs ad | 1 g |

MANUFACTURING PROCEDURE

Dissolve the Propylene Glycol and Monobasic Sodium Phosphate in a specified amount of Purified water at 80°-90° C. A weighed quantity of White Petrolatum, Cetomacrogol 1000, Cetyl Alcohol and Stearyl Alcohol are heated to 70°-75° C., and uniformly mixed. The melted waxes are added to the aqueous portion with stirring while cooling to 45°-50° C. The drug is slurried in a portion of Cetamacrogol dissolved in a specified amount of water. The active slurry is milled, then added to the formula while stirring. The cream is cooled to room temperature.

| Formulation 4 Lotion | |
|---|---|
| | mg/g |
| Drug | 20.0 |
| Propylene Glycol, USP | 350.0 |
| Alcohol, USP | 350.0 |
| Hydroxypropylcellulose | 2.5 |
| Purified Water qs ad | 1 g |

MANUFACTURING PROCEDURE

Dissolve the drug in Propylene Glycol heated to 50°-60° C. Cool to 30°-35° C. Add the Alcohol and Purified Water with stirring. Disperse the Hydroxypropylcellulose with stirring. Cool to room temperature.

| Formulation 5 Injectable Solution | |
|---|---|
| | mg/ml |
| Drug | 250.0 |
| Sodium Tartrate | 1.0 |
| Tartaric Acid | 4.0 |
| N,N-dimethylacetamide | 500.0 |
| Water for Injection qs ad | 1.0 ml |

MANUFACTURING PROCEDURE

Dissolve Sodium Tartrate and Tartaric Acid in a portion of Water for Injection. Dissolve the drug in N,N-dimethylacetamide. Mix both solutions and bring it to the final volume with Water for Injection. Aseptically filter the solution through a sterile 0.22 μm teflon (Millipore) membrane.

FORMULATION 6

Sterile Powder

For reconstitution with Water for Injection or normal saline to give final concentration of 100 mg/ml of drug in the solution intended for parenteral use.

| | |
|---|---|
| Drug (lyophilized) | 1.0 g |

MANUFACTURING PROCEDURE

Make a suitable slurry of the drug with Water for Injection and lyophilize it.

| Formulation 7 Capsules | | | |
|---|---|---|---|
| Item Ingredient | mg/cap | mg/cap | mg/cap |
| 1. Drug | 25 | 50 | 250 |
| 2. Lactose Impalpable Powder | 222 | 197 | 185 |
| 3. Corn Starch | 50 | 50 | 60 |
| 4. Magnesium Stearate | 3.0 | 3.0 | 5.0 |
| TOTAL | 300 mg | 300 mg | 500 mg |

MANUFACTURING PROCEDURE

Mix Item Nos. 1, 2 and 3 in a suitable mixer. Using a suitable mill, pass the mixture through a No. 40 screen. Add Item No. 4 and mix for 3-5 minutes. Encapsulate the mixture in two-piece hard gelatin capsules, using a suitable capsulating machine.

| Formulation 8 Tablets | | | |
|---|---|---|---|
| Item Ingredient | mg/Tab. | mg/Tab. | mg/Tab. |
| 1. Drug, Micronized | 25 | 50 | 250 |
| 2. Lactose, Impalpable Powder | 202.0 | 177.0 | 234 |
| 3. Microcrystalline Cellulose | 30.0 | 30.0 | 60.0 |
| 4. Corn Starch (10% paste in Water) | 10.0 | 10.0 | 20.0 |
| 5. Corn Starch | 30.0 | 30.0 | 30.0 |
| 6. Magnesium Stearate | 3.0 | 3.0 | 6.0 |
| TOTAL | 300 mg. | 300 mg. | 600 mg. |

MANUFACTURING PROCEDURE

Mix Item Nos. 1, 2 and 3 in a suitable blender. Add Item No. 4 and mix until a damp mass is formed. Using a suitable mill, pass the damp mass through a coarse sieve (e.g. No. 6) to yield the granules. Dry the granules for 8-16 hours at 40°-50° C. Mill the dried granules using a suitable mill through a No. 20 sieve. Add Item No. 5 to the milled granules and mix for 5 to 10 minutes. Mix further for 3-5 minutes after the addition of Item No. 6. Compress the mixture into a tablet using a suitable tablet press.

The processes described hereinabove are illustrated in detail hereinbelow in the Preparations and Examples which should not be construed as limiting the scope of my invention, equivalents of the specific disclosure herein will be obvious to those skilled in the art and are contemplated as included within the concept of my invention.

EXAMPLE 1

D-(THREO)-1-p-NITROPHENYL-2-DICHLOROACETAMIDO-3-FLUORO-1-PROPANOL

A. D-(Threo)-1-p-Nitrophenyl-2-Phthalimido-1,3-Propanediol

Add D-(threo)-1-p-nitrophenyl-2-amino-1,3-propanediol (21.2 gms., 0.1 mole), triethylamine (15 ml.) and phthalic anhydride (14.8 gms., 0.1 mole) to toluene (600 ml.) in a flask equipped with an overhead stirrer and a Dean-Stark water collector. Stir the reaction mixture at reflux temperature for 4 hours, cool with stirring to about 50° C., then add ethanol (300 ml.). Stir at room temperature for 1 hour, then allow the reaction mixture to remain at room temperature for 18 hours. Separate the resultant white precipitate by filtration, wash the filtrate with ethanol and dry to obtain D-(threo)-1-p-nitrophenyl-2-phthalimido-1,3-propanediol, yield 28.4 gms. (83% theory); m.p. 228°–229° C. (decomp.). Mass Spectrum: $(M^+ +1)$ 343; pmr: (dmso-$d_6$): $\delta$6.93–8.33 (aromatic hydrogens); 5.93 (d, J=4.0 Hz, benzylic OH); 5.27 (M, H-1); 4.83 (broad t, primary OH); 3.77–4.62 (m, $CH_2$); 3.5 (m, H-2).

B. D-(Threo)-1p-Nitrophenyl-2-Phthalimido-3-Fluoro-1-Propanol

To a stirring solution of D-(threo)-1p-nitrophenyl-2-phthalimido-1,3-propanediol (42.76 gms., 0.125 moles) in dry tetrahydrofuran (800 ml.) maintained at 0° C., add dropwise diethylaminosulfurtrifluoride (17.5 ml.). Stir the reaction mixture at 0° C. for 30 minutes, then allow the reaction mixture to warm to room temperature and stir at room temperature for an additional 5 hours. Evaporate the tetrahydrofuran in vacuo and chromatograph the resultant residue on a column of silica gel (2 kg.) eluting with a mixture of chloroform: ethanol (99:1). Combine the homogenous eluates containing the desired product as determined by thin layer chromatography and evaporate in vacuo to a residue of D-(threo)-1-p-nitrophenyl-2-phthalimido-3-fluoro-1-propanol, yield 32 gms. (74.4% theory). Further purify by crystallization from ethyl acetate: petroleum ether; m.p. 188°–190° C.; $[\alpha]_D^{26}$ −55.6° (c, 1 in dimethylformamide); Mass Spectrum: $(M^+ +1)$ 345; $M^+$ 344; pmr: (dmso-$d_6$):$\delta$7.70–8.42 (aromatic hydrogens); 6.20 (d, J=4.0 Hz, benzylic OH); 5.3 (m, H-1); 4.1–4.95 (m, $CH_2F$, H-2); Analysis Calculated for: $C_{17}H_{13}N_2O_5F$: C, 59.29; H, 3.80; N, 8.13; F, 5.52%. Found: C, 59.17; H, 3.93; N, 7.80; F, 5.40%.

C. D-(Threo)-1-p-Nitrophenyl-2-Amino-3-Fluoro-1-Propanol

Heat a mixture of D-(threo)-1-p-nitrophenyl-2-phthalimido-3fluoro-1-propanol (25.8 gms., 5 mmols), hydrazine hydrate (99%, 4 gms., 80 mmols), and ethanol (460 ml.) at reflux temperature for 4 hours, then let the reaction mixture stand at room temperature for 18 hours. Separate the solids by filtration and wash with a little ethanol. Concentrate the combined filtrate and ethanol washings in vacuo and extract the resultant residue with a chloroform: ethanol mixture (90:10) (700 ml.). Combine the chloroform: ethanol extracts and evaporate in vacuo to 18.1 g. of a residue comprising D-(threo)-1p-nitrophenyl-2-amino-3-fluoro-1-propanol, which can be used without further purification in the procedure described in the following example.

To prepare an analytical sample, chromatograph the foregoing residue on silica gel eluting with chloroform:

methanol: ammonium hydroxide (30:5:0.1). Combine the like fractions containing the desired product as determined by thin layer chromatography and evaporate the combined eluates to a residue comprising D-(threo)-1-p-nitrophenyl-2-amino-3-fluoro-1-propanol; m.p. 145°–147° C.; $[\alpha]_D^{26}$ −59° (c, 0.3 in dimethylformamide). Mass Spectrum: (M+ +1) 215, pmr; (dmso-d$_6$); δ 7.42–8.30 (aromatic hydrogens); 4.78 (d, J=4.0 Hz, H-1); 3.8–4.78 (m, CH$_2$); 2.8–3.3 (m, H-2). Analysis Calculated for: C$_9$H$_{11}$N$_2$O$_3$F: C, 50.47; H, 5.18; N, 13.08%. Found: C, 50.86; H, 5:53; N, 12.70%.

D. D-(Threo)-1-PNitrophenyl-2-Dichloroacetamido-3-Fluoro-1-Propanol

To D-(threo)-1-p-nitrophenyl-2-amino-3-fluoro-1-propanol prepared as described in Example 1C (18.1 gms.) add 80 ml. of a solution containing methyl dichloroacetate and 7 ml. of methanol. Heat the reaction mixture at 100° C. for 4 hours. Monitor the progress of the reaction by thin layer chromtography adding about 1 ml. of triethylamine as the reaction proceeds slowly. Remove the solvents in vacuo and wash the resultant residue with petroleum ether (200 ml.). Dissolve the washed residue in chloroform (about 700 ml.), concentrate in vacuo, and chromatograph the resultant residue on a column of silica gel (2 kg.) eluting with chloroform: ethanol (98:2). Pour the like fractions containing the desired product as determined by thin layer chromatography and evaporate the combined fractions in vacuo to a residue comprising D-(threo)-1-p-nitrophenyl-2-dichloroacetamido-3-fluoro-1-propanol, yield 19.9 gms. (81.5% theory). Further purify by dissolving the residue in chloroform (200 ml.) (concentrating to a volume of about 100 ml.) and adding petroleum ether (about 300 ml.). Separate the resultant precipitate by filtration to obtain purified D-(threo)-1-p-nitrophenyl-2-dichloroacetamido-3-fluoro-1-propanol, yield 16.6 gms.; m.p. 103°–104° C.; $[\alpha]_D^{26}$ −23.4° (c, 0.3 in dimethylformamide). Mass Spectrum: M+325: pmr: (dmso-d$_6$), δ 8.62 (d, J=9.0 Hz, NH); 7.54–8.30 (aromatic hydrogens); 6.5 (s, CHCl$_2$); 6.2 (d, J=4.0 Hz, benzylic OH); 4.0–5.2 (m, CH$_2$F, H-1 and H-2); Analysis Calculated for: C$_{11}$H$_{11}$N$_2$O$_4$FCl$_2$: C, 40.64; H, 3.41; N, 8.62; Cl, 21.81; F, 5.84%. Found, C, 41.22; H, 3.74; N, 8.51; Cl, 21.06; F, 6.07%.

EXAMPLE 2

D-(THREO)-1-p-Nitrophenyl-2-Difluoroacetamido-3-Fluoro-1-Propanol

To D-(threo)-1-p-nitrophenyl-2-amino-3-fluoro-1-propanol (0.428 gms., 2 mmol) add ethanol (5 ml.) ethyl difluoroacetate (0.5 gms.). Heat the reaction mixture at reflux temperature for 2 hours, then remove the solvent in vacuo and chromatograph the resultant residue on silica gel (50 gms.) eluting with chloroform:ethanol (95:5). Combine the like fractions containing the desired product as determined by thin layer chromatography and evaporate the combined fractions in vacuo to a residue (0.47 g.) comprising D-(threo)-1-p-nitrophenyl-2-difluoroacetamido-3-fluoro-1-propanol, yield 80% theory; m.p. 97°–98° C.; Mass Spectrum: (M+ +1), 293; pmr: (dmso-d$_6$); δ 8.8 (d, J=8.0 Hz, NH), 7.49–8.32 (aromatic hydrogens); 6.12 (t, J=54.0 Hz, CHF$_2$); 6.10 (d, J=4.0 Hz, benzylic OH); 4.05–5.05 (m, CH$_2$F, H-1 and H-2).

EXAMPLE 3

D-(Threo)-1-p-Nitrophenyl-2-Trifluoroacetamido-3-Fluoro-1-Propanol

In a manner similar to that described in Example 2, treat D-(threo)-1-p-nitrophenyl-2-amino-3-fluoro-1-propanol in ethanol with ethyl trifluoroacetate. Isolated and purify the resultant products in a manner similar to that to obtain D-(threo)-1-p-nitrophenyl-2-trifluoroacetamido-3-fluoro-1-propanol; m.p. 123°–124° C.; Mass Spectrum: m/e 152

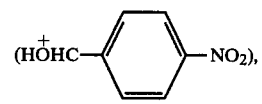

158 (F$_3$CCONH=CHCH$_2$F). pmr: (dmso-d$_6$); δ 9.5 (d, J=9.0 Hz, NH); 7.5–8.3 (aromatic hydrogen); 6.1 (d, J=4.0 Hz, benzylic OH); 4.1–5.3 (m, CH$_2$, H-1 and H-2).

EXAMPLE 4

D-(Threo)-1-p-Nitrophenyl-2-Acetamido-3-Fluoro-1-Propanol

Method A

To D-(threo)-1-p-nitrophenyl-2-amino-3-fluoro-1-propanol (0.428 g, 2 mmol), add ethanol (5 ml.) and with stirring add acetic anhydride (0.3 g, 3 mmol.). After 30 minutes at room temperature, remove the solvents in vacuo and chromatograph the residue and isolate the product in a manner similar to that described in Example 2 to obtain D-(threo)-1-p-nitrophenyl-2-acetamido-3-fluoro-1-propanol.

Method B

To D-(threo)-1-p-nitrophenyl-2-amino-3-fluoro-1-propanol (0.428 g., 2 mmol.), add ethanol (5 ml.) and triethylamine (0.202 g., 2 mmol.). Cool the solution to 5° C. with stirring and then add, dropwise, acetyl chloride (0.157 g., 2 mmol.). After 30 minutes at room temperature, isolate and purify the resultant product in a manner similar to that described in method A to obtain the title compound.

EXAMPLE 5

Other D-(Threo)-1-p-Nitrophenyl-2-Acylamido-3-Fluoro-1-Propanols

A. 2-Polyhalogenoacetamido and 2-α,α-Dihalogenopropionylamido Derivatives

In a manner similar to that described in Example 2, treat D-(threo)-1-p-nitrophenyl-2-amino-3-fluoro-1-propanol in methanol or ethanol with each of the following acetic acid or propionic acid esters:

(1) Methyl trichloroacetate,
(2) Methyl dibromoacetate,
(3) Methyl dichlorofluoroacetate,
(4) Methyl α,α-difluoropropionate,
(5) Methyl α,α-dichloropropionate,
(6) Methyl chlorodifluoroacetate.

Isolate and purify each of the resulting products in a manner similar to that described in Example 2 to obtain, respectively, (1) D-(threo)-1-p-nitrophenyl-2-trichloroacetamido-3-fluoro-1-propanol, (2) D-(threo)-1-p-nitrophenyl-2-dibromoacetamido-3-fluoro-1-propanol,
(3) D-(threo)-1-p-nitrophenyl-2-dichlorofluoroacetamido-3-fluoro-1-propanol,
(4) D-(threo)-1-p-nitrophenyl-2-$\alpha,\alpha$-difluoropropionamido-3-fluoro-1-propanol,
(5) D-(threo)-1-p-nitrophenyl-2-$\alpha,\alpha$-dichloropropionamide-3-fluoro-1-propanol,
(6) D-(threo)-1-p-nitrophenyl-2-dichlorofluoroacetamido-3-fluoro-1-propanol.

B. 2-Monohalogenoalkanoylamido and 2-$\alpha,\beta$-Dihalogenopropionoylamido Derivatives In a manner similar to that described in Example 4 (method B), treat D-(threo)-1-p-nitrophenyl-2-amino-3-fluoro-1-propanol in methanol or ethanol with each of the following acetic acid or propionic acid chlorides:
(7) Fluoroacetyl chloride,
(8) Chloroacetyl chloride,
(9) Bromoacetyl chloride,
(10) Iodoacetyl chloride,
(11) Propionyl chloride,
(12) $\alpha$-Fluoropropionyl chloride,
(13) $\alpha$-Chloropropionyl chloride,
(14) $\alpha$-Bromopropionyl chloride,
(15) $\alpha$-Iodopropionyl chloride,
(16) $\beta$-Chloropropionyl chloride,
(17) $\beta$-Bromopropionyl chloride,
(18) $\beta$-Iodopropionyl chloride,
(19) $\alpha,\beta$-Dichloropropionyl chloride,
(20) $\alpha,\beta$-Difluoropropionyl chloride, Isolate and purify each of the resulting products in a manner similar to that described in Example 2 to obtain, respectively,
(7) D-(threo)-1-p-nitrophenyl-2-fluoroacetamido-3-fluoro-1-propanol,
(8) D-(threo)-1-p-nitrophenyl-2-chloroacetamido-3-fluoro-1-propanol,
(9) D-(threo)-1-p-nitrophenyl-2-bromoacetamido-3-fluoro-1-propanol,
(10) D-(threo)-1-p-nitrophenyl-2-Iodoacetamido-3-fuoro-1-propanol,
(11) D-(threo)-1-p-nitrophenyl-2-propionamido-3-fluoro-1-propanol,
(12) D-(threo)-1-p-nitrophenyl-2-$\alpha$-fluoropropionamido-3-fluoro-1-propanol,
(13) D-(threo)-1-p-nitrophenyl-2-$\alpha$-chloropropionamido-3-fluoro-1-propanol,
(14) D-(threo)-1-p-nitrophenyl-2-$\alpha$-bromopropionamido-3-fluoro-1-propanol,
(15) D-(threo)-1-p-nitrophenyl-2-$\alpha$-iodopropionamido-3-fluoro-1-propanol,
(16) D-(threo)-1-p-nitrophenyl-2-$\beta$-chloropropionamido-3-fluoro-1-propanol
(17) D-(threo)-1-p-nitrophenyl-2-$\beta$-bromopropionamido-3-fluoro-1-propanol,
(18) D-(threo)-1-p-nitrophenyl-2-$\beta$-iodopropionamido-3-fluoro-1-propanol,
(19) D-(threo)-1-p-nitrophenyl-2-$\alpha,\beta$-dichloropropionamido-3-fluoro-1-propanol,
(20) D-(threo)-1-p-nitrophenyl-2-$\alpha,\beta$-difluoropropionamido-3-fluoro-1-propanol.

EXAMPLE 6

D-(Threo)-1-p-Methylsulfonylphenyl-2-Dichloroacetamido-3-Fluoro-1-Propanol

A. D-(Threo)-1-p-Methylsulfonylphenyl-2-Phthalimido-1,3-Propanediol

Suspend thiamphenicol (71 gms., 200 mmols) in water (300 ml.) containing concentrated hydrochloric acid (25 ml.). Stir the reaction mixture at reflux temperature for 6 hours, then evaporate to dryness in vacuo. Add toluene (100 ml.) to the resultant residue and evaporate. Repeat this procedure again and dry the residue comprising 1-p-methylsulfonylphenyl-2-amino-1,3-propanediol hydrochloride. Stir the foregoing dried residue in toluene (1400 ml.), then add with stirring triethylamine (29.9 gms.) and phthalic anhydride (44 gms.). Heat the reaction mixture at reflux temperature for 6 hours using a Dean-Stark water remover. Cool the reaction mixture, evaporate the solvent in vacuo, then dissolve the resultant residue in ethyl acetate (1.5 liters), wash the ethyl acetate solution with 1 N hydrochloric acid (800 ml.), then extract the hydrochloric acid washes twice with ethyl acetate (500 ml.), then combine the ethyl acetate solution with the original organic solution. Dry the combined ethyl acetate solutions over sodium sulfate and evaporate to dryness. Stir the resultant residue in ethanol (300 ml.), then set aside for 2 hours. Separate the resulting solid by filtration, wash the filtrate with a small quantity of ethanol and dry to give D-(threo)-1-p-methylsulfonylphenyl-2-phthalimido-1,3-propanediol (yield=35 gms.).

To obtain additional product, evaporate the combined ethanol filtrates in vacuo, dissolve the resultant residue in ethyl acetate, wash the ethyl acetate solution with 5% aqueous sodium bicarbonate, dry the ethyl acetate over sodium sulfate, then evaporate in vacuo. Triturate the resultant residue with ethanol, and filter to obtain additional D-(threo)-1-p-methylsulfonylphenyl-2-phthalimido-1,3-propanediol (additional yield=7.3 gms.); m.p. 209°–211° C.; Mass Spectrum m/e 190 (Pht $\overset{+}{N}$=CHCH$_2$OH), 186 (CH$_3$SO$_2$C$_6$H$_5$CH$_2$OH).

B. D-(Threo)-1-p-Methylsulfonylphenyl-2-Phthalimido-3-Fluoro-1-Propanol

Add diethylamine sulfurtrifluoride (25 ml.) dropwise to a stirred suspension of D-(threo)-1p-methylsulfonylphenyl-2-phthalimido-1,3-propanediol (66 gms., 0.176 mmol) in tetrahydrofuran (750 ml.) maintained at 0° C. with external cooling. After the addition is complete, stir for 30 minutes at 0° C. and then for 6 hours at room temperature. Set aside in the refrigerator overnight. Remove the solvent by evaporation in vacuo and chromatograph the resultant residue on a silica gel column (4 kg.) eluting with chloroform:ethanol (99:1). Combine the like fractions containing the desired product as determined by thin layer chromatography, and evaporate the combined fractions in vacuo to a residue of D-(threo)-1-p-methylsulfonylphenyl-2-phthalimido-3-fluoro-1-propanol, yield 24 gms.; m.p. 166°–168° C.; Mass Spectrum: m/e 192 (Pht $\overset{+}{N}$=CHCH$_2$F), 186 (CH$_3$SO$_2$C$_6$H$_5$CH$_2$OH); pmr: (dmso-d$_6$), $\delta$ 7.6–8.3 (aromatic hydrogens); 6.1 (d, J=4.0 Hz, benzylic OH); 3.95–5.4 (m, H-1, H-2 and CH$_2$F); 3.23 (s, SO$_2$CH$_3$).

C. D-(Threo)-1-p-Methylsulfonylphenyl-2-Amino-3-Fluoro-1-Propanol

Add hydrazine hydrate (99%, 0.16 gms.) to a solution of D-(threo)-1-p-methylsulfonylphenyl-2-phthalimido-3-fluoro-1-propanol (1.14 gms., 3 mmol) in ethanol (20 ml.). Heat at reflux temperature for 4 hours, cool to room temperature and remove the resultant solids by fraction. Evaporate the filtrate to a residue comprising D-(threo)-1-p-methylsulfonylphenyl-2-amino-3-fluoro-1-propanol.

D. D-(Threo)-1-p-Methylsulfonylphenyl-2-Dichloroacetamido-3-Fluoro-1-Propanol

Dissolve the D-(thero)-1-p-methylsulfonylphenyl-2-amino-3-fluoro-1-propanol prepared in Example 6C in methanol (5 ml.) and add methyl dichloroacetate (1 gm.). Heat the reaction mixture at reflux temperature for 2 hours, remove the solvents by evaporation in vacuo and extract the resultant residue with a mixture of chloroform:ethanol (75:25) (100 ml.). Evaporate the organic solvent extracts in vacuo and chromatograph the resultant residue on a silica gel column (90 gms.) eluting with a mixture of chloroform:ethanol (93:7). Combine the like eluates containing the desired product as determined by thin layer chromatography and evaporate in vacuo to a residue of D-(threo)-1-p-methylsulfonylphenyl-2-dichloroacetamido-3-fluoro-1-propanol, yield 0.5 gms.; m.p. 153°–154° C.; Mass Spectrum: M+ 358 pmr: (dmso-$d_6$) δ 8.3 (d, J=8.0 Hz, NH); 7.18–7.75 (aromatic hydrogens); 6.43 (s, CO$\underline{C}$HCl$_2$); 6.07 (d, J=4.0 Hz, benzylic OH); 3.9–5.1 (m, H-1, H-2 and $\underline{C}$H$_2$F); 3.14 (s, SO$_2$$\underline{C}$H$_3$).

EXAMPLE 7

D-(Threo)-1-p-Methylsulfonylphenyl-2-Difluoroacetamido-3-Fluoro-1-Propanol

Dissolve the D-(threo)-1-p-methylsulfonylphenyl-2-amino-3-fluoro-1-propanol prepared in Example 6C in ethanol (5 ml.) and add ethyl difluoroacetate (1 gm.). Heat the reaction mixture at reflux temperature for 2 hours, remove the solvents by evaporation in vacuo and extract the resultant residue with a mixture of chloroform:ethanol (75:25, 100 ml.). Evaporate the combined extracts in vacuo and chromatograph the resultant residue on silica gel (90 gms.) eluting with a mixture of chloroform:ethanol (93:7). Combine the like fractions containing the desired product as determined by thin layer chromatography and evaporate in vacuo to obtain D-(threo)-1-p-methylsulfonylphenyl-2-difluoroacetamido-3-fluoro-1-propanol, m.p. 141°–142° C.; Mass Spectrum: (M+ +1) 326; pmr (dmso-$d_6$) δ 8.88 (d, J=8.0 Hz, NH); 7.5–8.1 (aromatic hydrogens); 6.2 (t, J=54 Hz, CO$\underline{C}$HF$_2$); 6.07 (d, J=4.0 Hz, benzylic OH); 3.7–5.1 (m, H-1, H-2 and $\underline{C}$H$_2$F); 3.2 (s, SO$_2$$\underline{C}$H$_3$).

EXAMPLE 8

Other D-(Thero)-1-p-Methylsulfonylphenyl-2-Acylamido-3-Fluoro-1-Propanols

A. In a manner similar to that described in Example 6D, treat D-(threo)-1-p-methylsulfonylphenyl-2-amino-3-fluoro-1-propanol in methanol with methyl trifluoroacetate, and with each of the acetic acid and propionic acid ester starting compounds of Example 5A. Isolate and purify each of the resulting products in a manner similar to that described to obtain, respectively, D-(threo)-1-p-methylsulfonylphenyl-2-trifluoroacetamido-3-fluoro-1-propanol,
D-(threo)-1-p-methylsulfonylphenyl-2-trichloroacetamido-3-fluoro-1-propanol,
D-(threo)-1-p-methylsulfonylphenyl-2-dibromoacetamido-3-fluoro-1-propanol,
D-(threo)-1-p-methylsulfonylphenyl-2-dichlorofluoroacetamido-3-fluoro-1-propanol,
D-(threo)-1-p-methylsulfonylphenyl-2-α,α-difluoropropionamido-3-fluoro-1-propanol,
D-(threo)-1-p-methylsulfonylphenyl-2-α,α-dichloropropionamido-3-fluoro-1-propanol, and
D-(threo)-1-p-methylsulfonylphenyl-2-chlorodifluoroacetamido-3-fluoro-1-propanol.

B. In a manner similar to that described in Example 4 (method B), treat D-(threo)-1-p-methylsulfonylphenyl-2-amino-3-fluoro-1-propanol in methanol or ethanol with each of the acetic acid and propionic acid chloride starting compounds of Example 5B. Isolate and purify each of the resulting products in a manner similar to that described to obtain, respectively, D-(threo)-1-p-methylsulfonylphenyl-2-fluoroacetamido-3-fluoro-1-propanol,
D-(threo)-1-p-methylsulfonylphenyl-2-chloroacetamido-3-fluoro-1-propanol,
D-(threo)-1-p-methylsulfonylphenyl-2-bromoacetamido-3-fluoro-1-propanol,
D-(threo)-1-p-methylsulfonylphenyl-2-iodoacetamido-3-fluoro-1-propanol,
D-(threo)-1-p-methylsulfonylphenyl-2-propionamido-3-fluoro-1-propanol,
D-(threo)-1-p-methylsulfonylphenyl-2-α-fluoropropionamido-3-fluoro-1-propanol,
D-(threo)-1-p-methylsulfonylphenyl-2-α-chloropropionamido-3-fluoro-1-propanol,
D-(threo)-1-p-methylsulfonylphenyl-2-α-bromopropionamido-3-fluoro-1-propanol,
D-(threo)-1-p-methylsulfonylphenyl-2-α-iodopropionamido-3-fluoro-1-propanol,
D-(threo)-1-p-methylsulfonylphenyl-2-β-chloropripionamido-3-fluoro-1-propanol,
D-(threo)-1-p-methylsulfonylphenyl-2-β-bromopropionamido-3-fluoro-1-propanol,
D-(threo)-1-p-methylsulfonylphenyl-2-β-iodopropionamido-3-fluoro-1-propanol,
D-(threo)-1-p-methylsulfonylphenyl-2-α,β-dichloropropionamido-3-fluoro-1-propanol,
D-(threo)-1-p-methylsulfonylphenyl-2-α,β-difluoropionamido-3-fluoro-1-propanol.

EXAMPLE 9

D-(Threo)-1-p-Methylthiophenyl-2-Dichloroacetamido-3-Fluoro-1-Propanol

A. D-(Threo)-1-p-Aminophenyl-2-Phthalmido-3-Fluoro-1-Propanol

Dissolve a solution of D-(threo)-1-p-nitrophenyl-2-phthalimido-3-fluoro-1-propanol (11 gms., 32 mmol) in a solution of dioxane (120 ml.) isopropanol (60 ml.) and water (10 ml.) in a 500 ml. hydrogenation flask. Add 10% palladium-on-charcoal (1 gm.) and concentrated hydrochloric acid (3 ml.) and hydrogenate at 50 psi. Monitor the hydrogenation until all the starting material is converted to the corresponding p-aminophenyl derivative ($R_f$=0.49, silica gel thin layer chromatography, dichloromethane:acetone (90:10)). Remove the catalyst by filtration and wash the catalyst with isopropanol (20 ml.). Concentrate the combined filtrate and isopropanol washings in vacuo, and dissolve the resultant residue in 1 molar sodium hydroxide (30 ml.). Extract the aqueous solution several times with dichloromethane, dry the combined extracts over anhydrous magnesium sulfate and concentrate. Crystallize the resultant residue from anhydrous ethanol:diethyl ether and filter and dry the resultant precipitate to obtain D-(threo)-1-p-aminophenyl-2-phthalimido-3-fluoro-1-propanol, yield=6.2 gms. (19.7 mmol, 62% theory); m.p. 145.5°–147° C.; mass spectrum: M+ 314; Analysis Calculated for: $C_{17}H_{15}O_3N_2F$: C, 64.97; H, 4.81; N, 8.91; F, 6.05. Found: C, 65.23; H, 4.96; N, 8.79; F, 5.75.

B. D-(Threo)-1-p-Methylthiophenyl-2-Phthalimido-3-Fluoro-1-Propanol

To a solution of D-(threo)-1-p-aminophenyl-2-phthalimido-3-fluoro-1-propanol (3 gms., 9.6 mmol) in methylene chloride (60 ml.) cooled to 0° C., add a solution of nitrosyl chloride in methylene chloride (11 ml., 70 mg. per ml.). Stir at 0° C. for 20 minutes. Add sodium thiomethylate (0.8 gms.) and ethanol (10 ml.) and stir at room temperature for 18 hours. Add additional sodium thiomethylene (0.2 gms.) and stir for one hour. Filter the reaction mixture and evaporate the filtrate to a residue comprising D-(threo)-1-p-methylthiophenyl-2-phthalimido-3-fluoro-1-propanol, which is used without further purification in the procedure of Example 9C.

C. D-(Threo)-1-p-Methylthiophenyl-2-Amino-3-Fluoro-1-Propanol

Dissolve the D-(threo)-1-p-methylthiophenyl-2-phthalimido-3-fluoro-1-propanol prepared in Example 9B in absolute ethanol (20 ml.) and add hydrazine hydrate (0.55 ml.). Heat at reflux temperature for 3 hours, then filter.

The filtrate containing D-(threo)-1-p-methylthiophenyl-2-amino-3-fluoro-1-propanol is used without further purification in the procedure of following Example 9D.

D. D-(Threo)-1-p-Methylthiophenyl-2-Dichloroacetamido-3-Fluoro-1-Propanol

Add methyl dichloroacetate (1.4 ml.) to the filtrate containing D-(threo)-1-p-methylthiophenyl-2-amino-3-fluoro-1-propanol prepared in Example 9C. Heat the raction mixture at reflux temperature for 2 hours, evaporate in vacuo and chromatograph the resultant residue on a silica gel column (90 gms.) eluting with methylene chloride:2-propanol:concentrated ammonium hydroxide (28%) (90:6:0.1). Combine the like fractions containing the desired product as determined by thin layer chromatography and evaporate the combined like eluates to a residue of D-(threo)-1-p-methylthiophenyl-2-dichloroacetamido-3-fluoro-1-propanol, yield = 1.1 gm.; mass spectrum: M+ 325, 153 ($CH_3SC_6H_4CH_2OH$).

EXAMPLE 10

D-(Threo)-1-Phenyl-2-Dichloroacetamido-3-Fluoro-1-Propanol

A. D-(Threo)-1-Phenyl-2-Phthalimido-3-Fluoro-1-Propanol

To a solution of D-(threo)-1-p-aminophenyl-2-phthalimido-3-fluoro-1-propanol (800 mg.) in methyl chloride (40 ml.) cooled to 0° C., add a solution of nitrosyl chloride in methylene chloride (3 ml., 70 mg. per ml.). Stir at 0° C. for 20 minutes, then separate the resultant precipitate by filtration and wash with methylene chloride to obtain the diazonium chloride salt from D-(threo)-1-p-aminophenyl-2-phthalimido-3-fluoro-1-propanol.

Dissolve the foregoing diazonium chloride salt in cold water (6 ml.) and quickly add the solution to 50% aqueous hypophosphorous acid (1.6 gms.) which has been previously cooled in a water bath. Allow the reaction mixture to warm to 25° C., then stir for 3 hours at 25° C. Extract the reaction mixture with methylene chloride (a total of 75 ml.), wash the combined methylene chloride extracts with dilute aqueous sodium bicarbonate, dry the methylene chloride solution over anhydrous magnesium sulfate, and evaporate to a residue comprising D-(threo)-1-phenyl-2-phthalimido-3-fluoro-1-propanol (yield 0.7 gms.), which is used without further purification in the procedure of Example 10B.

B. D-(Threo)-1-Phenyl-2-Amino-3-Fluoro-1-Propanol

Dissolve the D-(threo)-1-phenyl-2-phthalimido-3-fluoro-1-propanol prepared in Example 10A in absolute ethanol (10 ml.), add hydrazine hydrate (0.12 ml.) and heat at reflux temperature for 3 hours, then filter, and evaporate the filtrate to a residue comprising D-(threo)-1-phenyl-2-amino-3-fluoro-1-propanol, which is used without further purification in the procedure of following Example 10C.

C. D-(Threo)-1-Phenyl-2-Dichloroacetamido-3-Fluoro-1-Propanol

Dissolve the D-(threo)-1-phenyl-2-amino-3-fluoro-1-propanol prepared in Example 10B in methanol (6 ml.), add methyl dichloroacetate (14 ml.), and heat at reflux temperature, keeping the reaction mixture at pH 8 by the addition of triethylamine. Continue refluxing until all the starting material has been consumed as evidenced by thin layer chromatography on silica gel using chloroform:ethanol (97:3) as solvent, then concentrate the reaction mixture. Purify the resultant residue by chromatography on a silica gel column (2.8×30 cm.) eluting with chloroform:ethanol (99:1), taking 4 ml. fractions, 2 minutes per tube. Combine the like fractions containing the desired product as determined by thin layer chromatography and evaporate to a residue comprising D-(threo)-1-phenyl-2-dichloroacetamido-3-fluoro-1-propanol (yield 0.4 gms.) (1.43 mmol, 56% theory). Mass Spectrum: 280 (M++1); 282 (M++3); 107 ($H\overset{+}{O}=CH$—phenyl); pmr: (dmso-d$_6$) δ 5.86 (benzylic OH); 6.51 ($Cl_2\underline{CH}$—); 7.31 (phenyl).

EXAMPLE 11

D-(Threo)-1-p-Methylsulfinylphenyl-2-Dichloroacetamido-3-Fluoro-1-Propanol

To a solution of D-(threo)-1-p-methylthiophenyl-2-dichloroacetamido-3-fluoro-1-propanol (compound of Example 9) (910 mg., 2.8 mmol) in 95% dioxane (10 ml.) at 0° C., add sodium metaperiodate (600 mg.) and stir for 30 minutes. Destroy any excess sodium metaperiodate by addition of ethylene glycol until the reaction mixture is negative to starch-iodide paper. Add dioxide (twice the volume of the reaction mixture) and filter the resultant precipitated salts. Evaporate the dioxane filtrate and to the resultant residue add chloroform:ethanol (3:1, 50 ml.), then filter the resultant solid, and wash with chloroform:ethanol (3:1). Combine the filtrate and washings, evaporate and chromatograph the resultant residue on a 15 gm. silica gel column (1.8×30 ml.) eluting with chloroform:ethanol (99:1). Combine the like fractions containing the desired product as determined by thin layer chromatography and evaporate to a residue comprising D-(threo)-1-p-methylsulfinylphenyl-2-dichloroacetamido-3-fluoro-1-propanol (yield 247 mg.). Mass Spectrum: 342 (M++1); 344 (M++3); 169 ($HO=CHC_6H_4SOCH_3$). pmr: (dmso-d$_6$) δ 5.98 (d, J=3.0 Hz, benzylic OH); 6.45 (s, $Cl_2\underline{CH}CO$—); 7.58 (s, aromatic); 2.67 (s, $\underline{CH_3}SO_2$).

EXAMPLE 12

D-(Threo)-1-p-Nitrophenyl-2-(R,S-Chlorofluoroacetamido)-3-Fluoro-1-Propanol

Add triethylamine (0.2 ml.) to a solution of D-(threo)-1-p-nitrophenyl-2-amino-3-fluoro-1-propanol (prepared as described in Example 1C) (1.1 gm.) and ethyl chlorofluoroacetate (0.5 ml.) in ethanol (14 ml.). Heat at reflux temperature under a blanket of nitrogen for 2 hours. Add an additional amount of ethyl chlorofluoroacetate (0.5 ml.) and continue heating until the reaction is essentially complete as indicated by the absence of starting compound as determined by thin layer chromatography using a mixture of chloroform and methanol (9:1 by volume) as the solvent system. Evaporate the solvents in vacuo and chromatograph the resultant residue on silica gel (40 gms.) using chloroform as the eluant. Collect like fractions containing the desired product as determined by thin layer chromatography, evaporate to dryness in vacuo to obtain D-(threo)-1-p-nitrophenyl-2-(R,S-chlorofluoroacetamido)-3-fluoro-1-propanol (yield 0.97 gm.). Mass Spectrum: M+309, m/e 157, 156, 153, 152, 139, 137, 136, 122, 106, 105, 102, 94, 78, 77, 76, 70, 67, 62, 60, 52, 51 and 50.

EXAMPLE 13

D-(Threo)-1-p-Nitrophenyl-2-Dichlorodeuterioacetamido-3-Fluoro-1-Propanol

Add triethylamine (0.7 ml.) to a stirred solution of D-(threo)-1-p-nitrophenyl-2-dichloroacetamido-3-fluoro-1-propanol (0.75 gm.) in methyl alcohol-d (i.e., $CH_3OD$) (7 ml.) and stir the solution at room temperature for 18 hours. Concentrate in vacuo and dry the resultant residue in vacuo over phosphorus pentoxide overnight. Dissolve the residue in methanol (5 ml.) and evaporate to dryness. Repeat this procedure once more. Crystallize the resultant product from an ethyl acetate/n-hexane mixture to obtain D-(threo)-1-p-nitrophenyl-2-dichlorodeuterioacetamido-3-fluoro-1-propanol (yield 0.59 gm.). Mass Spectrum (M++1) 326. PMR (dmso-$d_6$): δ8.6 (d, J=8 Hz, NH), 7.96 (ABq, J=10 Hz, aromatic hydrogens), 6.15 (d, J=5 Hz, benzylic OH).

In similar manner, treat each of the products of Examples 2, (5A2), (5B12), (5B13), (5B14), (5B15), (5B19), (5B20), 6, 7, 9, 10, 11, 12 and the 2-dihalogenoacetamido and α-halogenopropionamido products of Examples 8A and 8B with methyl alcohol-d to obtain the respective 2-dihalogenodeuterioacetamido and the 2-(α-halogenodeuteriopropionamido) derivatives.

EXAMPLE 14

Sodium D-(Threo)-1-p-Nitrophenyl-2-Dichloroacetamido-3-Fluoro-1-Propyl Hemi-Succinate To D-(threo)-1-p-nitrophenyl-2-dichloroacetamido-3-fluoro-1-propanol (1.3 gm., 4 mmols) in dioxane (12 ml.) add succinic anhydride (0.92 gm., 8 mmols) and triethylamine (2.4 ml.). Allow the solution to stand at room temperature for 6 hours, then evaporate to a small volume and dissolve the resultant residue in chloroform (200 ml.). Wash the chloroform solution with dilute hydrochloric acid then wash with water; dry over magnesium sulfate, filter and evaporate. Recrystallize the resultant residue from diethylether to obtain D-(threo)-1-p-nitrophenyl-2-dichloroacetamido-3-fluoro-1-propylsuccinate; yield 950 mg. (56% theory).

Dissolve D-(threo)-1-p-nitrophenyl-2-dichloroacetamido-3-fluoro-1-propanol succinate (850 mg., 2 mmols) in water, add sodium bicarbonate (168 mg., 2 mmols), stir for 15 minutes, filter, add water to the filtrate, then evaporate to a residue comprising sodium D-(threo)-1-p-nitrophenyl-2-dichloroacetamido-3-fluoro-1-propyl hemi-succinate; yield 800 mg. PMR ($D_2O$): δ2.68 (4H, m, $CH_2$ of the hemisuccinate), 6.1l (1H, d, J=3.0 Hz, benzylic H), 6.28 (1H, s, $CHCl_2$), 7.8 (4H, center of AA, BB quartet, aromatic hydrogens)

EXAMPLE 15

D-(Threo)-1-p-Nitrophenyl-2-Azidoacetamido (And 2-Methylsulfonylacetamido)-3-Fluoro-1-Propanols Treat D-(threo)-1-p-nitrophenyl-2-amino-3-fluoro-1-propanol in a manner similar to that described in Example 2 but utilizing each of ethyl azidoacetate and ethyl methylsulfonylacetate instead of ethyl difluoroacetate to obtain, respectively, D-(threo)-1-p-nitrophenyl-2-azidoacetamido-3-fluoro-1-propanol, and D-(threo)-1-p-nitrophenyl-2-methylsulfonylacetamido-3-fluoro-1-propanol, having the following physical constants: PMR (dmso-$d_6$): δ2.91 (3H, s, C$\underline{H}_3SO_2CH_2$), 4.04 (2H, s, $CH_3SO_2C\underline{H}_2$), 6.08 (1H, d, J=5.0 Hz, benzylic OH), 7.86 (4H, center of AA', BB' quartet, aromatic hydrogens).

EXAMPLE 16

D-(Threo)-1-p-Nitrophenyl-2-Dichloroacetamido-3-Fluoro-1-Propanol Prepared From D-(Threo)-2-Dichloromethyl-4-p-Nitrophenylhydroxymethyl-Δ2-oxazoline Stir a mixture of D-(threo)-2-dichloromethyl-4-para-nitrophenyl-hydroxymethyl-Δ$^2$-oxazoline (1 gm.), lithium fluoride (0.5 gm.) and liquid hydrogen fluoride in a teflon-lined bomb for 24 hours. Evaporate off the gaseous hydrogen fluoride into a suitable trap, then dissolve the resultant residue in chloroform and wash the chloroform solution twice with water, then dry over magnesium sulfate and evaporate. Chromatograph the resultant residue on silica gel using chloroform as the eluant. Collect like fractions containing the desired product as determined by thin layer chromatography and evaporate in vacuo to obtain a residue comprising D-(threo)-1-para-nitrophenyl-2-dichloroacetamido-3-fluoro-1-propanol.

EXAMPLE 17

D-(Threo)-1-p-Methylsulfonylphenyl-2-Difluoroacetamido-3-Fluoro-1-Propanol Glycinate Trifluoroacetic Acid Salt Dissolve D-(threo)-1-p-methylsulfonylphenyl-2-difluoroacetamido-3-fluoro-1-propanol (1.29 gms.), N-p-methoxybenzyloxycarbonyl glycine (1.1 gm.), N,N-dicyclohexylcarbodiimide (1.1 gm.) and pyridine (0.5 ml.) in acetonitrile (50 ml.). Stir for 4 hours, then evaporate in vacuo at 50° C. and chromatograph the resultant residue over silica gel (200 gms.) eluting with 1% ethanol/chloroform. Collect the like fractions containing pure D-(threo)-1-p-methylsulfonylphenyl-2-difluoroacetamido-3-fluoro-1-propanol N-p-methoxybenzyloxycarbonylglycinate as determined by thin layer chromatography and evaporate. Dissolve the resultant residue under anhydrous conditions in trifluoroacetic acid (20 ml.). Add ethyl ether (100 ml.) to the solution and separate the resultant precipitate by filtration. Dissolve the precipitate in water, filter and lyophilize the aqueous solution to obtain D-(threo)-1-p-methylsulfonylphenyl-2-difluoroacetamido-3-fluoro-1-propanol glycinate trifluoroacetic acid salt, yield 1.23 gms.; pmr (dmso-$d_6$), δ 7.84 (ABq, J=8 Hz, aromatic hydrogen),
δ 6.25 (d, J=3 Hz, H-1),
δ 6.05 (t, J=53 Hz, $CH_2F$),
δ 4.07 (s, glycyl C$\underline{H}_2$),
δ 3.17 (s, $SO_2C\underline{H}_3$).

EXAMPLE 18

D-(Threo)-1-p-Methylsulfonylphenyl-2-Difluoroacetamido-3-Fluoro-1-Propanol Ornithate Trifluoroacetic Acid Salt Treat D-(threo)-1-p-methylsulfonylphenyl-2-difluoroacetamido-3-fluoro-1-propanol in a manner similar to that described in Example 17 but use di-N-p-methoxybenzyloxycarbonyl ornithine (2.3 gms.) instead of p-methoxybenzyloxycarbonyl glycine to obtain D-(threo)-1-p-methylsulfonylphenyl-2-difluoroacetamido-3-fluoro-1-propanol ornithate trifluoroacetic acid salt, yield 0.84 gms., pmr (dmso-d$_6$), δ 7.87 (ABq, J=8 Hz, aromatic hydrogen),
δ 6.19 (d, J=3 Hz, H-1),
δ 6.07 (t, J=53 Hz, CH$_2$F),
δ 3.2 (s, SO$_2$CH$_3$),
δ 1.92 (broad, ornithine CH$_2$—CH$_2$),
δ 3.0 (broad, ornithine CH).

EXAMPLE 19

D-(Threo)-1-p-Methylsulfonylphenyl-2-Difluoroacetamido-3-Fluoro-1-Propanol Lysinate Trifluoroacetic Acid Salt Treat-D-(threo)-1-p-methylsulfonylphenyl-2-difluoroacetamido-3-fluoro-1-propanol in a manner similar to that described in Example 17, but use di-N-p-methoxybenzyloxycarbonyl lysine (3.06 gms.) instead of p-methoxybenzyloxycarbonyl glycine to obtain D-(threo)-1-p-methylsulfonylphenyl-2-difluoroacetamido-3-fluoro-1-propanol lysinate trifluoroacetic acid salt, yield 3.1 gms., pmr (dmso-d$_6$), δ 7.81 (ABq, J=8 Hz, aromatic hydrogens),
δ 6.19 (d, J=3 Hz, H-1),
δ 6.08 (t, J=53 Hz, CH$_2$E),
δ 3.23 (s, SO$_2$CH$_3$),
δ 2.90 (broad, lysine CH),
δ 1.90 (broad, lysine CH$_2$)

EXAMPLE 20

The Sulfuric Acid Salts of D-(Threo)-1-p-Methylsulfonylphenyl-2-Difluoroacetamido-3-Fluoro-1-Propanol Glycinate and of D-(Threo)-1-p-Methylsulfonyl-2-Difluoroacetamido-3-Fluoro-1-Propanol Ornithate (1) Dissolve the trifluoroacetic acid salt product of Example 17 in tetrahydrofuran and add 0.5 molar equivalents of sulfuric acid. Evaporate the tetrahydrofuran in vacuo, then re-dissolve the resultant residue in tetrahydrofuran and evaporate again. Repeat this procedure until all the trifluoroacetic acid is displaced by sulfuric acid as evidenced by cmr data to obtain D-(threo)-1-p-methylsulfonylphenyl-2-difluoroacetamido-3-fluoro-1-propanol glycinate sulfuric acid salt.

(2) Treat the trifluoroacetic acid salt of each of Examples 18 and 19 in a manner similar to that described above to obtain D-(threo)-1-p-methylsulfonylphenyl-2-difluoroacetamido-3-fluoro-1-propanol ornithate sulfuric acid salt and D-(threo)-1-p-methylsulfonylphenyl-2-difluoroacetamido-3-fluoro-1-propanol lysinate sulfuric acid salt, respectively.

I claim:

1. A D-(threo-1-aryl-2-amino-3-fluoro-1-propanol of the following formula:

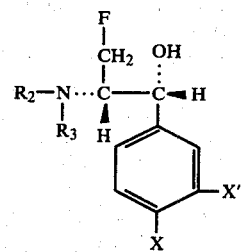

wherein R$_2$ and R$_3$ are hydrogen or together with the attached nitrogen form phthalimido or succinimido;
each of X and X' is a member selected from the group consisting of NO$_2$, SO$_2$R$_1$, SOR$_1$, SR$_1$, SONH$_2$, SO$_2$NH$_2$, SONHR$_1$, SO$_2$NHR$_1$, COR$_1$, OR$_1$, R$_1$, CN, halogen, hydrogen, phenyl, and phenyl substituted by halogen, NO$_2$, SO$_2$CH$_3$, R$_1$ or OR$_1$, wherein R$_1$ is methyl, ethyl n-propyl or isopropyl.

2. A compound of claim 1 wherein X' is hydrogen and X is NO$_2$, SO$_2$R$_1$, SOR$_1$ or SO$_2$HN$_2$.

3. A compound of claim 1 wherein R$_2$ and R$_3$ are hydrogen or together with the attached nitrogen form phthalimido, X' and Z are hydrogen, and X is NO$_2$, SO$_2$R$_1$, SOR$_1$ or SO$_2$NH$_2$.

4. The process for the preparation of a D-(threo)-1-aryl-2-acylamido-3-fluoro-1-propanol of the following formula:

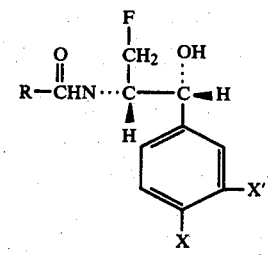

wherein R is a member selected from the group consisting of methyl or ethyl or a halogenated derivative thereof, dihalogenodeuteriomethyl, 1-halogeno-1-deuterioethyl, 1,2-dihalogeno-1-deuterioethyl, azidomethyl and methylsulfonylmethyl; each of X and X' is a member selected from the group consisting of NO$_2$, SO$_2$R$_1$, SOR$_1$, SR$_1$, SONH$_2$, SO$_2$NH$_2$, SONHR$_1$, SO$_2$NHR$_1$, COR$_1$, OR$_1$, R$_1$, CN, halogen, hydrogen, phenyl and phenyl substituted by halogen, NO$_2$, SO$_2$CH$_3$, R$_1$or OR$_1$, and wherein R$_1$ is methyl, ethyl, n-propyl or isopropyl;

which comprises the reaction of D-(threo)-1-aryl-2-N-protected-amino-1,3-propanediol with dialkylamine sulfur trifluoride in an inert organic solvent followed by removal of the N-protecting group in the thereby formed D-(threo)-1-aryl-2-N-protected-amino-3-fluoro-1-propanol; thence reaction of the resulting D-(threo)-1-aryl-2-amino-3-fluoro-1-propanol with a lower alkanoic acid derivative selected from acetic acid anhydride, acetyl chloride, propionic acid anhydride or propionyl chloride, a halogeno acetic acid chloride or anhydride in the presence of base, a halogeno propionic acid chloride of anhydride in the presence of base, or with a lower alkyl ester of an α,α-dihalogeno acetic acid or of an α,α-dihalogeno propionic acid ester in a lower alkanol.

5. The process of claim 4 wherein said dialkylamine sulfur trifluoride is diethylamino sulfur trifluoride and wherein said lower alkyl ester of a lower alkanoic acid is methyl dichloroacetate or ethyl difluoroacetate or ethyl chlorofluoroacetate whereby is prepared a D-(threo)-1-aryl-2-dichloroacetamido-3-fluoro-1-propanol, D-(threo)-1-aryl-2-difluoroacetamido-3-fluoro-1-propanol, or a D-(threo)-1-aryl-2-chlorofluoroacetamido-3-fluoro-1-propanol, respectively.

6. The process of claim 4 wherein said D-(threo)-1-aryl-2-N-protected-amino-1,3-propanediol is D-(threo)-1-p-nitro-phenyl-2-phthalimido-1,3-propanediol, said dialkylamine sulfur trifluoride is diethylamine sulfur trifluoride, wherein said lower alkyl ester of an alkanoic acid is methyl dichloroacetate, ethyl difluoroacetate or ethyl chlorofluoroacetate, whereby is formed, respectively, D-(threo)-1-p-nitrophenyl-2-dichloroacetamido-3-fluoro-1-propanol, D-(threo)-1-p-nitrophenyl-2-difluoroacetamido-3-fluoro-1-propanol, and D-(threo)-1-p-nitrophenyl-2-fluorochloroacetamido-3-fluoro-1-propanol.

7. The process of claim 4 wherein said D-(threo)-1-aryl-2-N-protected-amino-1,3-propanediol is D-(threo)-1-p-methylsulfonylphenyl-2-phthalimido-1,3-propanediol, said diethylamine sulfur trifluoride is diethylamine sulfur trifluoride and said lower alkyl ester of a lower alkanoic acid is methyl dichloroacetate, ethyl difluoroacetate, or ethyl chlorofluoroacetate, whereby is formed, respectively, D-(threo)-1-p-methylsulfonylphenyl-2-dichloroacetamido-3-fluoro-1-propanol, D-(threo)-1-p-methylsulfonylphenyl-2-difluoroacetamido-3-fluoro-1-propanol, and D-(threo)-1-p-methylsulfonylphenyl-2-fluorochloroacetamido-3-fluoro-1-propanol.

* * * * *